United States Patent [19]

Déprez

[11] Patent Number: 4,802,464
[45] Date of Patent: Feb. 7, 1989

[54] TRACTION DEVICE FOR OPERATING TABLES AND ORTHOPAEDIC SURGERY APPARATUS FOR SURGICAL OPERATIONS

[75] Inventor: Roland Déprez, Gentilly, France
[73] Assignee: Marzet-Aubry, Gentilly, France
[21] Appl. No.: 33,992
[22] Filed: Apr. 2, 1987

[30] Foreign Application Priority Data

Apr. 3, 1986 [FR] France .................................. 0604786

[51] Int. Cl.$^4$ .............................................. A61F 5/00
[52] U.S. Cl. ........................................ 128/71; 269/328
[58] Field of Search ............................ 128/69, 71, 33; 269/322, 323, 328

[56] References Cited

U.S. PATENT DOCUMENTS

| | | | |
|---|---|---|---|
| 2,283,549 | 5/1942 | Galbraith | 128/71 |
| 3,434,165 | 3/1969 | Keane | 128/71 X |
| 3,509,876 | 5/1970 | Pilz | 128/71 |
| 3,654,920 | 4/1972 | Staib | 128/71 |
| 4,144,880 | 3/1979 | Daniels | 128/71 |
| 4,360,009 | 11/1982 | Weisman | 128/71 |
| 4,527,555 | 7/1985 | Ruf | 269/322 X |

FOREIGN PATENT DOCUMENTS

1427080 3/1965 France .
2518400 9/1983 France .
2111834 7/1983 United Kingdom .

Primary Examiner—Edgar S. Burr
Assistant Examiner—Moshe I. Cohen
Attorney, Agent, or Firm—Shenier & O'Connor

[57] ABSTRACT

Traction device comprising:
a frame defining a median plane
a pelvis support connected to the frame and adjustable laterally with respect to said median plan,
two arms articulated in said median plane, the first arm being a central traction arm, articulated so as to be mobile horizontally and vertically, the second arm being a central counter-extension arm articulated so as to be mobile horizontally, said arms being provided with means for blocking in position and with traction means. The means for blocking the central arm comprises a clamping sleeve co-axial to the arm and manoeuvrable in rotation, passing through intersecting meridian slots of two spherical lunes articulated on orthogonal axes, the sleeve comprising two inverted threads cooperating with jaws mobile in translation on the sleeve and located on either side of the intersection of the lunes so as to cause, by moving them closer to or away from each other, the blocking by friction or unblocking of the arm.

9 Claims, 7 Drawing Sheets

TRACTION DEVICE FOR OPERATING TABLES AND ORTHOPAEDIC SURGERY APPARATUS FOR SURGICAL OPERATIONS

FIELD OF THE INVENTION

The present invention relates to traction devices for operating tables and orthopaedic surgery apparatus for surgical operations to be carried out principally on the lower limbs of a patient under the control of apparatus with radiogenic source.

BACKGROUND OF THE INVENTION

Orthopaedic surgery is often carried out on operating tables comprising traction systems, principally used for operations on the lower limbs of a patient, which are composed of traction arms comprising mechanical screw tractors. These traction arms are fixed on a frame which comprises the elements necessary for supporting the patient's pelvis. These traction arms may be articulated horizontally and vertically.

At the present time, orthopaedic surgery makes use of per-operatory radiological control in intensive manner. The control apparatus with radiogenic source, and particularly the luminance amplifiers, require easy access to the operative field.

The systems of articulation of the orthopaedic traction devices, which are generally voluminous and lie in the axis of the operative field, prevent maximum use of the apparatus with radiogenic source. Furthermore, the traction devices designed for maximum use of the apparatus with radiogenic source are not easy to handle and their traction arms are only partially articulated.

For example, British Patent No. 2 111 834 discloses a device comprising a frame; two lateral arms articulated on the frame so as to be horizontally mobile, the arms being provided with means for locking in position and traction means; and a pelvis support connected to the frame and adjustable laterally with respect to the median plane of the frame. In this device, the articulation of the arms allows only their horizontal displacement, which is insufficient to respond to all requirements in orthopaedic surgery. Moreover, the means for locking the arms, made in the form of clamping levers disposed at the level of the articulated joints, are of difficult access when the operative field is already encumbered with ancillary apparatus.

SUMMARY OF THE INVENTION

It is an object of the invention to propose a device whose traction arms are sufficiently manoeuvrable, whilst allowing maximum use of the control apparatus with radiogenic source, thanks to a maximum clearance of the operative field.

This object is attained by the invention thanks to a novel design in which the two lateral traction arms are replaced by two central arms, i.e. articulated in a median plane, one of the arms being a traction arm proper, intended for the limb to be operated on, and mobile horizontally and vertically, the other arm, which may be mobile horizontally only, simply being a counter-extension arm. Lateral displacement of the pelvis support makes it possible to move the limb to be operated on out of centre towards the right or towards the left with respect to the central traction arm.

This design has been made possible by taking into account the fact that, in practice, the surgeon must only operate on one of the patient's limbs during one operation; it is therefore possible to reserve for this sole limb a single arm provided with an articulation in all directions, and to provide for the limb not operated on a simple counter-extension arm, requiring only a simplified articulation.

The means for locking the central arm advantageously comprises a clamping sleeve coaxial to the arm and manoeuvrable in rotation, passing through intersecting meridian slots of two spherical lunes articulated on orthogonal axes, the sleeve comprising two inverted threads cooperating with jaws mobile in translation on the sleeve and located on either side of the intersection of the lunes so as to cause, by moving them closer to or away from each other, the locking by friction or unlocking of the arm.

A contact shoe is advantageously interposed between the lunes at the intersection thereof and the clamping sleeve is manoeuverable thanks to the rotation of a handle located at the end of the arm, transmitted by a control shaft.

These arrangements enable the articulation and the locking device to be made in a very compact form, completely clearing the operative field.

The traction arm advantageously comprises a tubular element associated with connecting rods and bars so as to form articulated parallelograms permanently maintaining parallelism with the arm of the tractor support of the traction means. Since, according to the invention, the patient's leg is no longer in the axis of the traction arm and therefore said deformable parallelograms are no longer in a vertical plane parallel to the patient's leg, the distance between the point of attachment of the tractor on the patient's foot and hip varies as a function of the displacement of the arm. It is then advantageous to use in combination with this tractor an electronic tension controller maintaining the force of traction constant, whatever the manipulation of the arm. Reference may usefully be made on this subject to Applicants' French patent application No. 2 578 418 filed on on Mar. 8, 1985, and corresponding to U.S. patent application Ser. No. 837,007 filed on Mar. 6, 1986.

The pelvis support is laterally adjustable thanks to a pivot connected to the frame and a catching system.

BRIEF DESCRIPTION OF THE INVENTION

The invention will be more readily understood on reading the following description with reference to the accompanying drawings, in which:

FIG. 6 shows a side view of the swivel joint of the principal arm.

DETAILED DESCRIPTION OF THE INVENTION

1. General description of the device of the invention.

Referring now to the drawings, the device of the invention comprises a compact frame 1, secured at one end 2 to an independent orthopaedic table.

Another end 3 of the frame 1 forms a substantially parallelepipedic cavity adapted to house the articulation of the central traction arm 4.

The median part of the frame 1 comprises bearings in which swivel an upper vertical pivot 5 intended for the pelvis support 6 and a lower vertical pivot 7 (FIG. 6) which effects articulation of the central counter-extension arm 8. Pivots 5 and 7 are on the same vertical axis 9 contained in the median vertical plane 10 of frame 1.

The pelvis support 6 is mounted on the pivot 5 by means which will be described in detail hereinafter, so that its receiving part, comprising the ring 11 and the upright 12, may be placed on one side or the other of the median plane 10 of the frame (cf. FIGS. 2 and 3).

The counter-extension arm 8 is mobile, thanks to its articulation on the pivot 7, in a horizontal plane. It may be locked thanks to means 13 and comprises traction means 14 at its end opposite the articulation.

Articulation of the central traction arm 4, housed in the cavity 3 of the frame, is effected by a universal joint centred in the median plane so as to allow the arm 4 movements in all directions. The arm 4 may be locked in any position by means 15 and also comprises traction means 16.

The articulation of the central traction arm is located slightly above the horizontal plane swept by the central counter-extension arm 8.

2. Operational principle of the device

Figure 1:
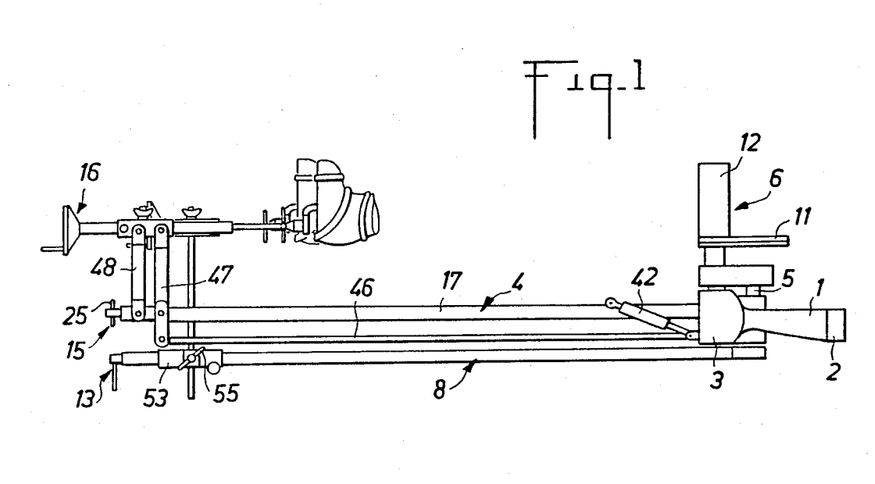
FIG. 1 shows a side view of the device according to the invention.
Figures 2, 3:
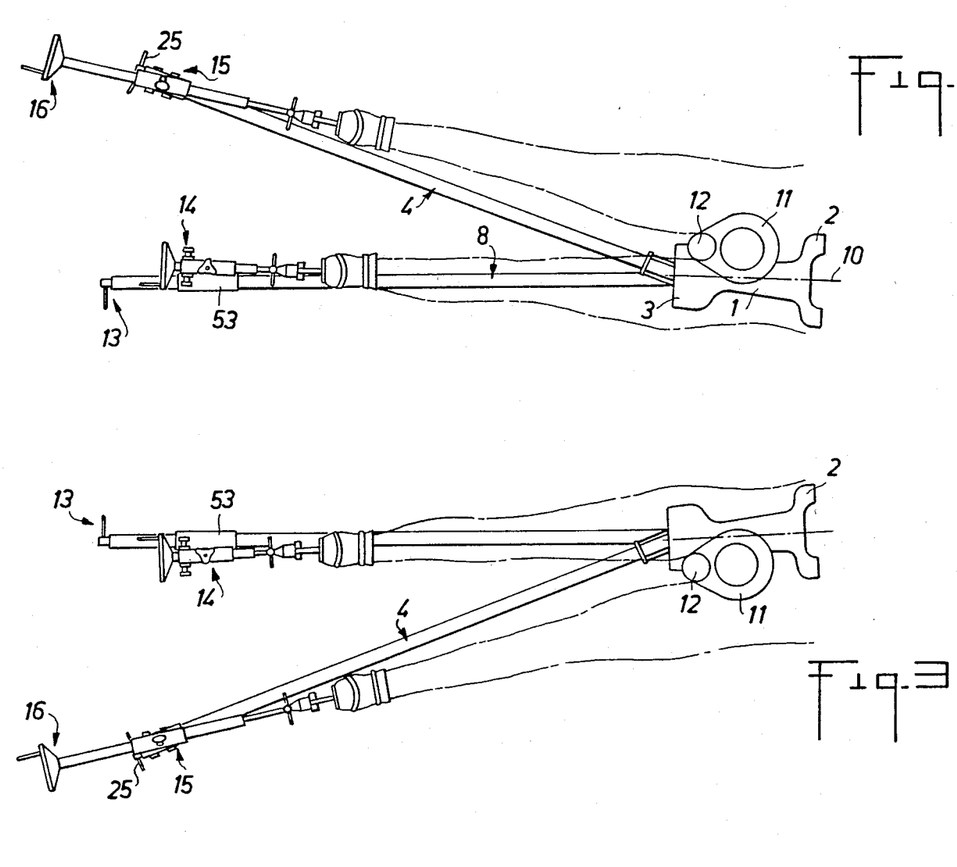
FIG. 2 shows a plan view of the device of FIG. 1; in this Figure, the position of the traction arm indicates that the operation is carried out on the right leg.
FIG. 3 shows a plan view of the device of FIG. 1; in this Figure, the position of the traction arm indicates that the operation is carried out on the left leg.

The central traction arm 4, intended for the leg to be operated on, may equally well receive the patient's right leg (FIG. 2) or left leg (FIG. 3). Lateral adjustment of the pelvis support 6 makes it easier to off-centre the leg to be operated on with respect to the median plane 10. The leg which is not to be operated on is fixed on counter-extension arm 8. The respective locking means 13 and 15 and the traction means 14 and 16 make it possible to choose the desired position and traction on the legs.

Figures 4, 5:
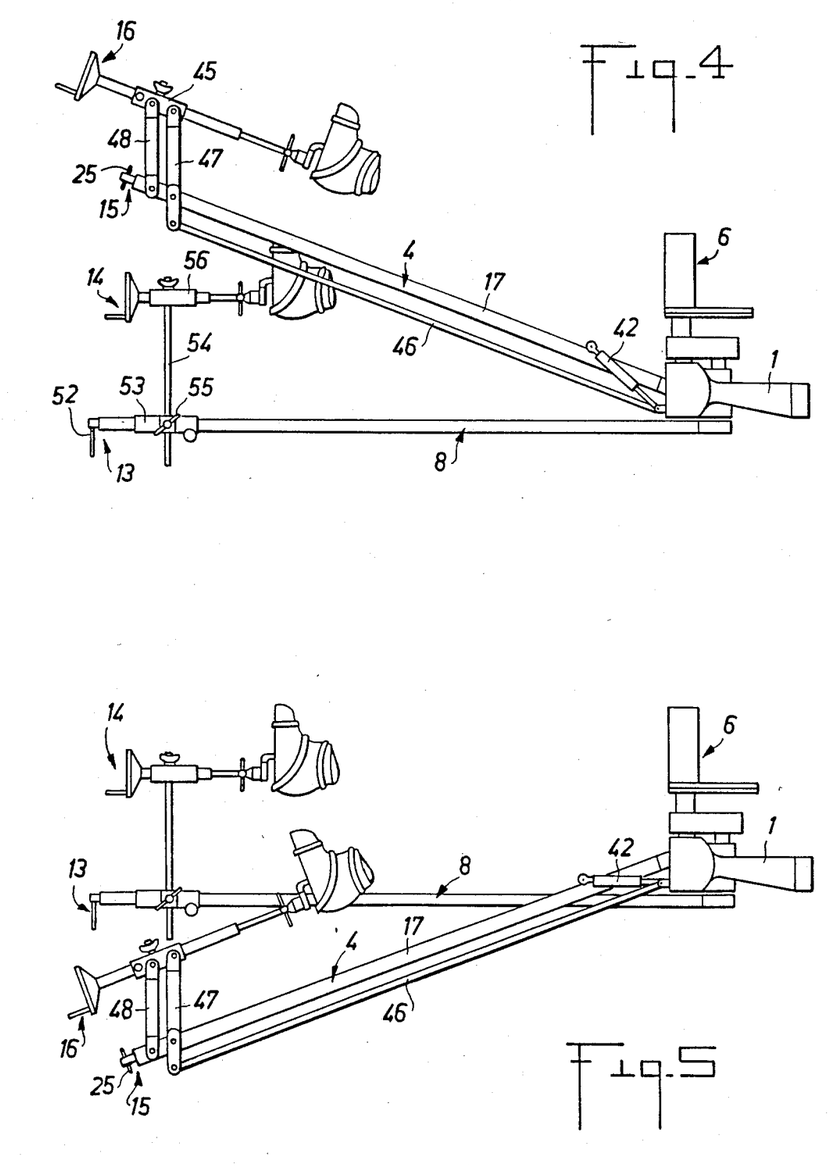
FIG. 4 shows a side view of the device, the traction arm being shown in "high" position.
FIG. 5 shows a side view of the device, the traction arm being shown in "low" position.
Figure 5:
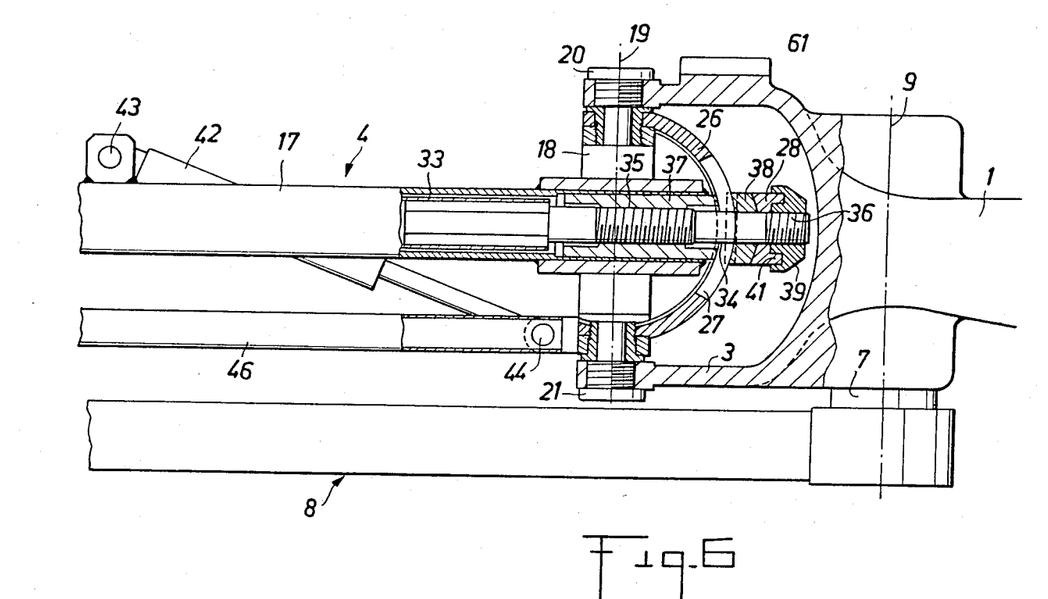

The bilateral nature of the device is obtained by interchanging the traction arm 4 and the counterextension arm 8. In view of the dimensions of the ends of arms 4 and 8, due to the locking means 13 and 15 and traction means 14 and 16, this permutation is effected by raising the arm 4 (FIG. 4) sufficiently for it to pass, during pivoting thereof, above the traction means 14 of arm 8.

3. Detailed description of the different members 3.1 The central traction arm 3.1.1 The articulation of the central traction arm Reference will be made to FIGS. 6 and 7.

Figure 7:
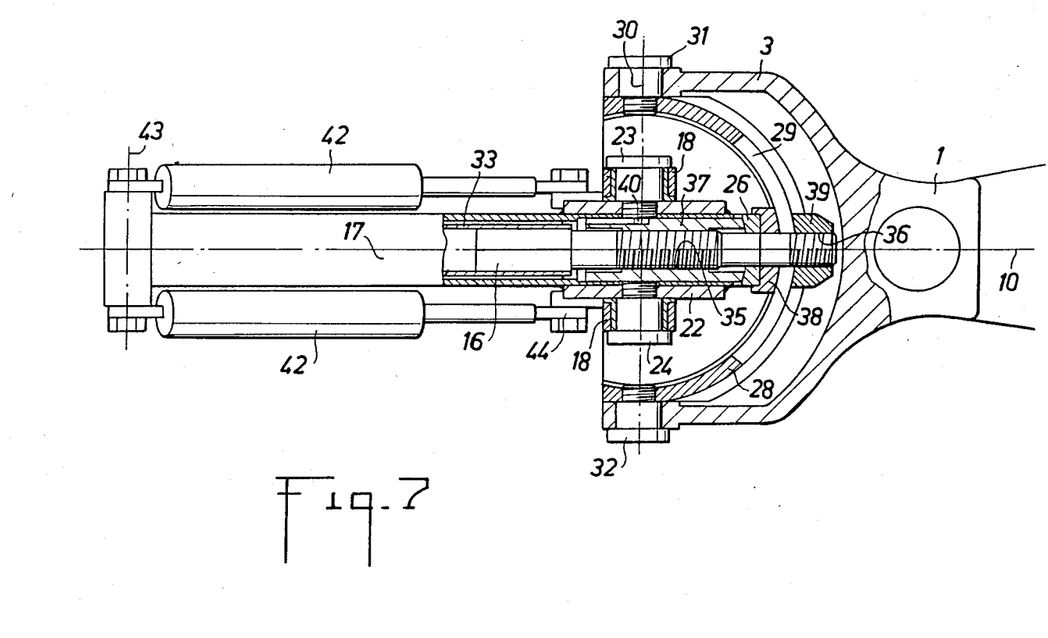
FIG. 7 shows a plan view of the swivel joint of the principal arm.

The arm 4 comprises a principal tubular element 17 articulated on a cross-piece 18. The cross-piece 18 pivots vertically about axis 19 thanks to journals 20, 21 housed in the upper and lower walls of the cavity 3 of the frame 1.

The end 22 of the element 17 bears lateral journals 23, 24 which enable it to pivot horizontally in the lateral arms of the cross-piece 18.

The whole constitutes a Universal joint.

3.1.2 The means for locking the traction arm

One of the original features of the invention resides in the design of the locking means compatible with the universal joint described hereinabove.

These means, adapted to be manoeuvred by the handle 25 located at the other end of the arm, are constituted as follows:

A first vertical spherical lune 26, or, to be more exact, a band in meniscal form, comprising a meridian slot 27, pivots freely about axis 19 (via journals 20, 21 serving for assembly of the cross-piece 18).

A second spherical lune 28, orthogonal to and of radius larger than the first, and comprising a meridian slot 29, is mounted to pivot freely about the horizontal axis 30, at right angles to the median plane 10, via journals 31, 32 passing through the lateral walls of the cavity 3.

The tubular element 17 of the arm 4 houses a control shaft 33, mounted to rotate and driven by the clamping handle 25. The shaft 33 extends on the side of the articulation of the arm by a clamping sleeve 34 comprising two threaded parts 35, 36 of opposite pitch.

The sleeve 34 passes through the orthogonal meridian slots 27 and 29, with the result that the first threaded part 35, located inside the lunes 26 and 28, cooperates in translation with an inner mobile jaw 37 and that the second threaded part 36, located outside said lunes, cooperates in translation with an outer mobile jaw 39. A contact shoe 38, traversed by the clamping sleeve 34, serves as brace between the two lunes 26 and 28. A pin 40 blocks the inner jaw 37 in rotation, whilst ribs 41 of the lune 28 block the outer jaw 39, provided with corresponding grooves, in rotation.

The locking mechanism is as follows:

Rotation of the clamping sleeve 34, provoked on the handle 25 and transmitted by the control shaft 33, brings about an inverted translation of each of the jaws 37, 39. Approach thereof towards lunes 26, 28 provokes clamping, their moving away provokes loosening.

When the jaws are loosened, pivoting of the lunes and guiding of the clamping sleeve along the meridian slots enable the mechanism not to hinder the freedom of movement of the arm 4, as long as the maximum angular extension allowed by the slots is not attained.

3.1.3. Pneumatic compensation of the traction arm

When the arm 4 is unlocked, the only force which is exerted thereon is that which results from its own weight and which stresses the arm downwardly.

In order to maintain the arm 4 in loosened position, without any intervention outside the apparatus, a pneumatic compensation system is provided. This system is constituted by two jacks 42, located on either side of the arm 4, articulated about a horizontal pivot 43 on the tubular element 17 and a horizontal pivot 44 connected to the cross-piece 18, with the result that the jacks 42 can follow all the movements of the element 17.

3.1.4. Traction means of the traction arm

The traction means 16 comprise a tractor support 45 maintained parallel to the arm 4 by an articulated mechanism.

This mechanism comprises on the one hand a connecting rod 46 articulated on the pivot 44 connected to the cross-piece 18 and on one end of a connecting bar 47 articulated on the tubular element 17 so as to compose a parallelogram deformable in a vertical plane.

Another end of the rod 47 is articulated on the tractor support 45, and a second rod 48 is also articulated on the tubular element 17 and the tractor support 45 so as to compose with the first rod 47 another articulated parallelogram deformable in a vertical plane.

In fact, these pieces are disposed in double, on either side of arm 4.

It is immediately seen that these articulated parallelograms ensure maintenance and constant parallelism of the tractor support 45.

Figure 8:
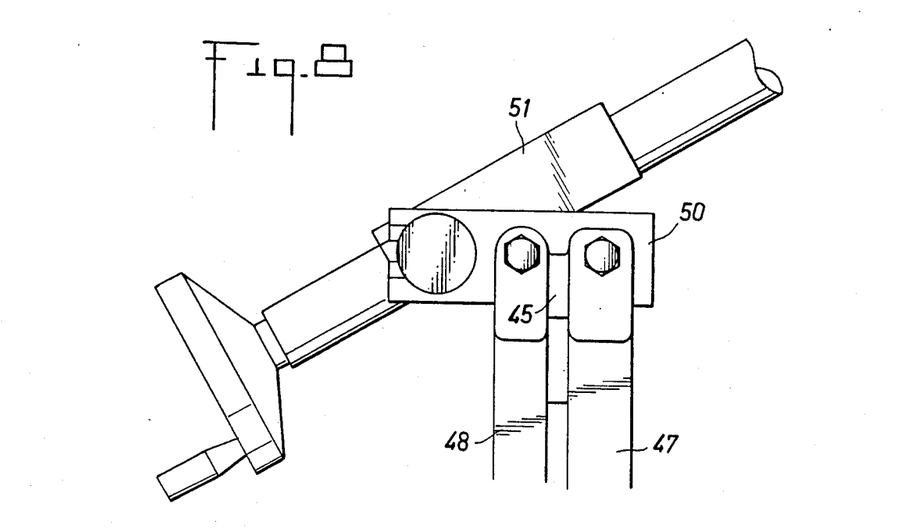
FIG. 8 shows a side view of the tractor support assembly.
Figure 9:
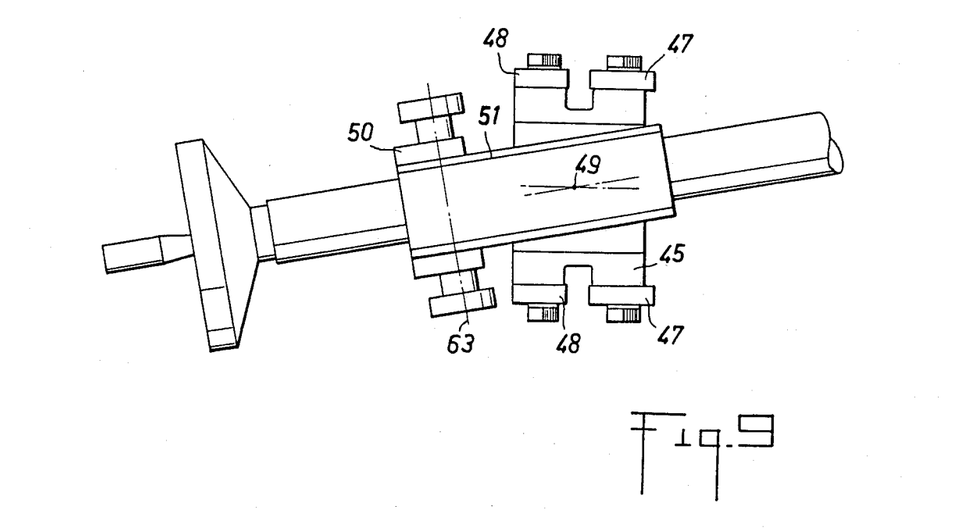
FIG. 9 shows a plan view of the tractor support assembly.
Figure 10:
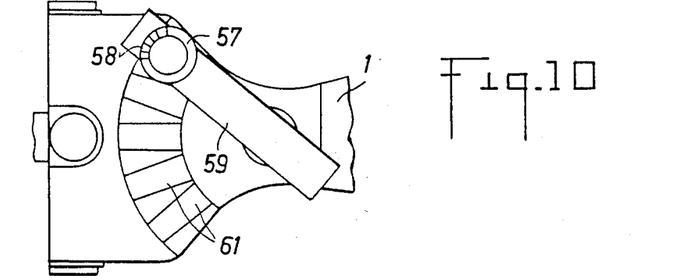
FIG. 10 shows a plan view of the notchable pelvis support; in this Figure, the pelvis is off-centred towards the right.

This latter comprises a cradle element fast with connecting rods 47, 48 (FIGS. 8 and 9) and which offers a pivot 49 to a piece 50 receiving the housing 51 of the tractor. The piece 50 is free to rotate in a plane parallel to the traction arm 4. The housing 51 is also mounted to pivot freely on a horizontal, transverse pin 63 of the piece 50. The tractor proper is conventional and does not need to be described.

4. The counter-extension arm

The arm 8 is mobile horizontally about pivot 7. Locking and unlocking thereof are controlled by a handle 52 acting via a control shaft on a locking jaw bearing on pivot 7.

The arm 8 bears a sliding support 53 adapted to be locked in any position over the length of the arm 8. A vertical sliding rod 54 is mounted on the support 53 so as to be adjustable in height and in angulation in a horizontal plane thanks to a locking screw 55. This rod 54 supports the housing 56 of the counter-extension tractor, which comprises a device for angulation in a vertical plane, similar to that of the tractor of the traction arm.

5. The pelvis support

The pelvis support 6 is articulated on a vertical pivot 5 in frame 1.

The ring 11 and column 12 cover a vertical spindle 57 provided with indexing notches 58 and borne by a horizontal arm 59 fast with the pivot 5.

On the lower face of arm 59, a catch 60 may be inserted in one or the other of the different notches 61 formed on the upper face of the frame 1.

Figure 11:
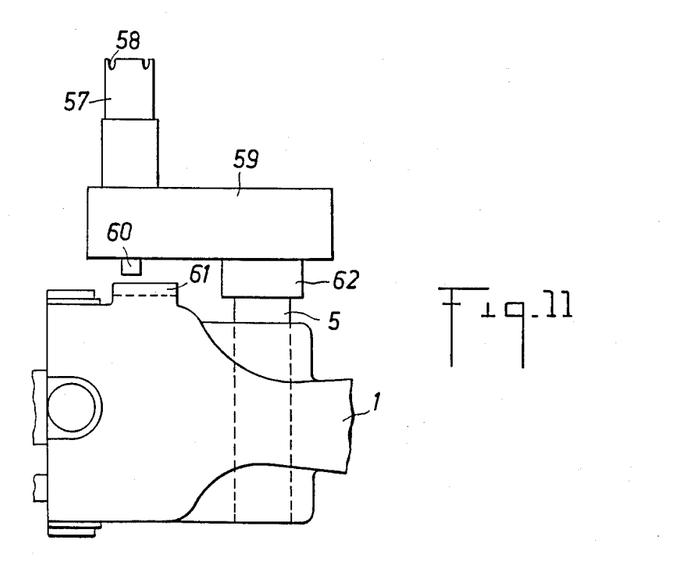
FIG. 11 shows a side view of the pelvis support in disengaged position.
Figure 12:
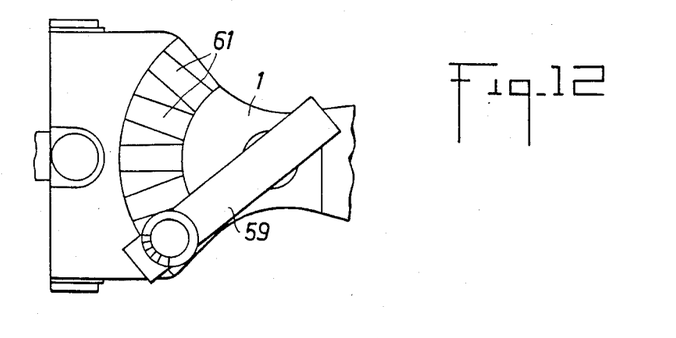
FIG. 12 shows a plan view of the notchable pelvis support; in this Figure, the pelvis is off-centred towards the left.

In order to displace the pelvis support from one lateral position to another, it suffices to disengage catch 60 from notches 61 (FIG. 11) and to pivot the arm 59 about pivot 5, then to engage the catch 60 again in the chosen notch 61. A shoulder 62 is provided for the arm 59 to abut against the frame 1 at a height compatible with the penetration of catch 60 in a notch 61. It then remains to reorient the ring 11 by pivoting about spindle 57.

What is claimed is:

1. A traction device for operating tables and orthopaedic surgery comprising:
    a frame defining a median vertical plane,
    a first arm being a central traction arm,
    a second arm being a central counter-extension arm,
    each of said arms being provided with traction means and means for locking said arms in position,
    means mounting said first arm on said frame for both horizontal movement around a first axis in said median plane and for vertical movement around a second axis perpendicular to said median plane,
    means mounting said second arm on said frame for only horizontal movement around a third axis in said median plane,
    a pelvis support,
    and means mounting said pelvis support on said frame for adjustment laterally with respect to said median plane.

2. The device of claim 1, wherein said first arm comprises a tubular element articulated on the frame by a universal joint.

3. The device of claim 2, wherein the means for locking said first arm comprise a clamping sleeve coaxial to said first arm and adapted to be manoeuvred in rotation, passing through intersecting meridian slots of two spherical lunes, articulated on orthogonal axes, the sleeve comprising two inverted threads cooperating with jaws mobile in translation on the sleeve and located on either side of the intersection of the lunes so as to bring about, by mutual approach or moving apart, locking by friction or unlocking of said first arm.

4. The device of claim 3, wherein a contact shoe is interposed between the lunes at the intersection thereof.

5. The device of claim 4, wherein the clamping sleeve is manoeuvrable thanks to the rotation of a handle located at the end of said first arm, transmitted by a control haft.

6. The device of claim 1, wherein said first arm comprises a tubular element associated with connecting rods and bars so as to form articulated parallelograms permanently maintaining parallelism with said first arm of a tractor support of said traction means.

7. The device of claim 1, wherein said first arm comprises pressure cylinders for compensating its own weight.

8. The device of claim 1, wherein said pelvis support mounting means comprises a pivot pin, means adjustably mounting said pivot pin on said frame and interengageable means on said pivot pin and said frame for releasably locking said pivot pin in its adjusted position.

9. A traction device as in claim 1 in which said pelvis support mounting means comprises an upper vertical pivot disposed coaxially with respect to said third axis.

* * * * *